United States Patent [19]

Davies

[11] 4,017,471

[45] Apr. 12, 1977

[54] IMMUNOLOGICAL COMPOUNDS

[75] Inventor: David Allen Lewis Davies, High Wycombe, England

[73] Assignee: G. D. Searle & Co., High Wycombe, England

[22] Filed: Sept. 15, 1975

[21] Appl. No.: 613,446

[52] U.S. Cl. .............................. 260/112 B; 424/177
[51] Int. Cl.² ............................................ A23J 1/06
[58] Field of Search ................. 260/112 B; 424/177

[56] References Cited

UNITED STATES PATENTS

| | | | |
|---|---|---|---|
| 3,639,558 | 2/1972 | Csizmas | 260/112 B |
| 3,709,868 | 1/1973 | Spector | 260/112 B |
| 3,903,262 | 9/1975 | Pappenhagen | 260/112 B |

*Primary Examiner*—Paul R. Michl
*Attorney, Agent, or Firm*—John J. McDonnell

[57] ABSTRACT

The present invention relates to an antitumor agent comprising p-di(2-chloroethyl)amino-L-phenylalanine or N,N-bis(2-chloroethyl)p-phenylenediamine hydrochloride bound to a tumor specific antibody by peptide bonds. The antitumor agent of the present invention is prepared by reacting a cytotoxic agent, p-di(2-chloroethyl)amino-L-phenylalanine or N,N-bis(2-chloroethyl)p-phenylenediamine hydrochloride with a tumor specific antibody in the presence of a water soluble carbodiimide such as 1-ethyl-3-(3-dimethylaminopropyl)-carbodiimide hydrochloride and thereby forming a peptide bond between the cytotoxic agent and the tumor specific antibody.

4 Claims, No Drawings

IMMUNOLOGICAL COMPOUNDS

The present invention relates to an antitumor agent comprising p-di(2-chloroethyl)amino-L-phenylalanine (Melphalan) or N,N-bis(2-chloroethyl)p-phenylenediamine bound to a tumor specific antibody by peptide bonds.

Thus cytotoxic agents of the formula

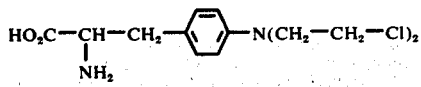

or

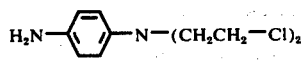

are reacted with tumor specific antibodies in the presence of a water soluble carbodiimide to form peptide bonds between the cytoxic agent and the tumor specific antibody.

Specific antisera are prepared by conventional techniques of immunization and collection of sera. These antisera are then absorbed with, for example, normal cells to remove those unwanted antibodies against cells other than the target cells. The remaining antibodies will be directed against predominantly the target cells of choice, for example, tumor cells. Their subsequent linkage to a toxic agent provides an effective, specific, cytotoxic agent, which may be directed towards a chosen target cell.

Tumor specific antibodies are for example raised against neoplastic tissue by techniques described by Ghose et al. British Medical Journal (1972) 3, 495–499. Thus, in a preferred embodiment antibodies against mouse EL4 lymphoma (EL4 immunoglobulin) are reacted with p-di(2-chloroethyl)amino-L-phenylalanine in the presence of 1-ethyl-3(3-dimethylaminopropyl-carbodiimide hydrochloride to provide a cytotoxic agent-tumor specific antibody complex having about 13 molecules of cytotoxic agent per molecule of antibody.

Antibodies against neoplasms of lymphatic and hematopoietic tissues including lymphosarcoma, chronic lymphatic leukemia, Hodgkin's disease, carcinoma of the ovary, breast and testicles, and other epithelial tissues and melanoma are tumor specific antibodies contemplated by the present invention. The globulan fraction anti to these tissues and absorbed with normal tissue is bound to a cytotoxic agent such as p-di(2-chloroethyl)amino-L-phenylalanine by 1-ethyl-3(3-dimethylaminopropyl)-carbodiimide.

It is essential to the present invention that after the complex is formed the tumor specific antibody retain its specificity and the cytotoxic agent retain its ability to alkylate. Both of these essentials are fulfilled by carbodiimide induced peptide bond formation wherein about 5–15 molecules of either of the above indicated cyctotoxic agents are linked to a suitable tumor specific antibody. The fulfillment of these essentials permits the tumor specific antibody to deliver the bound cytotoxic agent to the desired situs of activity.

The dosage will vary according to the tumor specific antibody, the amount and type of cytotoxic agent bound thereto, the extent of neoplastic growth, and individual tolerance to the tumor specific antibody-cytotoxic agent complex. Since toxic side effects of the cytotoxic agent are greatly reduced by binding to the tumor specific antibody large doses of bound cytotoxic agent may advantageously be administered. Doses of p-di(2-chloroethyl)amino-L-phenylalanine (Melphalan) described in Cuttings Handbook of Pharmacology, 4th edition, 1969, Appleton Century Crafts at page 139 may be increased 2–5 times.

The hereinafter set forth examples are intended to illustrate the present invention and are not intended to limit the invention in spirit or scope.

EXAMPLE 1

An antiserum is raised in rabbits against EL4 tumor cells (cells of a transplantable lymphoma from C57B1/6 strain mice). EL4 cells, withdrawn from mice, are injected intravenously into rabbits in three doses of $10^8$ cells per dose at intervals of 10 days. Ten days after the last dose the rabbit is bled and the serum collected. This serum is heated to 56° C for 30 minutes in order to destroy complement activity.

The collected serum is absorbed with normal mouse cells to leave tumor-specific antibodies. The serum is absorbed with a pool of mouse spleen cells, including at least some from mice of the C57B1/6 or similar strain. Repeated absorptions are made with the equivalent of ten spleens to one milliliter of serum, for 16 hours at 4° C with stirring, until there is no reactivity of the serum against normal C57B1/6 strain cells in conventional cytotoxicity tests. In the same test, and also in indirect immunofluorescence or agglutination tests, the same serum is reacted with EL4 tumor cells, to demonstrate the tumor-specificity of the serum prepared above.

The globulin fractional is precipitated from the serum by addition of saturated ammonium sulphate until the final concentration is 40%. The precipitated EL4 globulin (Ig) is redissolved in phosphate buffered saline to provide a final protein concentration of 30–50 mg/ml, as measured by the Biuret reaction.

A peptide linkage between an amino or carboxylic acid group present on certain cytotoxic drugs and corresponding groups on the antibody molecules, is prepared in the presence of carbodiimide, as described below.

The following reagents are prepared (A) 10 mls EL4 immunoglobulin solution at 57 mg/ml adjusted to pH 6.5 with HCL; (B) either (i) 57 mg N,N-bis(2-chloroethyl)p-phenylenediamine hydrochloride in 2 mls Dioxan, or (ii) 57 mg p-di(2-chloroethyl)amino-L-phenylalanine dissolved in 0.8 mls of an acid: ethanol mixture (92% ethanol containing 2% w/v HCl) then diluted with a buffer solution of 60% propylene glycol, containing 1.2% w/v di-potassium hydrogen phosphate, to reach a final pH of 6–6.5, (C) 114 mg 1-ethyl-3(3-dimethylaminopropyl)-carbodiimide HCl dissolved in 0.5 mls saline.

Reagents A, B and C are mixed rapidly for five seconds and the reaction stopped by the addition of 6 mls of 1M sodium acetate at pH 6.5. The resulting solution is dialysed against three changes of 0.3% sodium citrate solution over 24 hours, at 4° C in order to remove unlinked drug.

The drug-antibody complex is analyzed for protein content and alkylating activity. Protein content is measured using a conventional Biuret assay with bovine serum albumin as a standard. Alkylating activity is assayed using the Epstein method (Epstein. J, Rosenthal, R. W., and Ess. R. J., Anal. Chem. 27, 1434 (1955)).

The final preparation of N,N-bis(2-chloroethyl)p-phenylenediamine/antibody complex contains 12.2 mg EL4 immunoglobulin/ml and 122 ug N,N-bis(2-chloroethyl)p-phenylenediamine/ml. This represents a ratio of approximately 5.0 drug molecules per molecule of Ig. Similarly, the final solution of p-di(2-chloroethyl)amino-L-phenylalanine/antibody complex contains 13.9 mg EL4 immunoglobulin/ml and 380 ug p-di(2-chloroethyl)amino-L-phenylalanine/ml, representing a ratio of approximately 13.6 molecules per molecule antibody.

It is therefore possible to covalently link the present drugs to tumor specific antibodies by means of a peptide linkage. The activity of such drug/antibody complexes is shown in Example 2.

EXAMPLE 2

Use of Drug/Antibody Complexes

Drug/antibody complexes, prepared according to the methods described above, are used to protect mice against the lethal effects of the injection of EL4 tumor cells.

Groups of mice are injected intraperitoneally with approximately 10,000 lethal doses (5 × 10⁴) tumor cells collected from the abdomen of previously infected mice. Twenty four hours after the injection of cells, animals receive the first of four daily doses of therapeutic agent, or control agent, as outlined below.

1. Treatment with N,N-bis(2-chloroethyl)p-phenylenediamine/EL4 immunoglobulin complexes

| Treatment | 50% Mouse Survival (days) |
| --- | --- |
| Saline | 14.5 |
| Normal rat globulin/N,N-bis(2-chloroethyl) p-phenylenediamine (½ml doses containing 245 µg N,N-bis(2-chloroethyl)p-phenylenediamine and 7.0 mg normal rat globulin) | 14.5 |
| EL4 immunoglobulin alone (25 mg) | 24.5 |
| N,N-bis(2-chloroethyl)p-phenylenediamine/ EL4 immunoglobulin | 34.0 |

-continued

1. Treatment with N,N-bis(2-chloroethyl)p-phenylenediamine/EL4 immunoglobulin complexes

| Treatment | 50% Mouse Survival (days) |
| --- | --- |
| (1.4 ml doses containing 170 µg N,N-bis(2-chloroethyl)p-phenylenediamine and 17 mg EL4 immunoglobulin) | |

2. Treatment with p-di(2-chloroethyl)amino-L-phenylalanine/EL4 immunoglobulin complexes

| Treatment | 50% Mouse Survival (days) |
| --- | --- |
| Saline control | 15.5 |
| EL4 immunoglobulin alone (1 mg) | 26.6 days |
| p-di(2-chloroethyl)amino-L-phenylalanine/ EL4 immunoglobulin complex (760 µg p-di(2-chloroethyl)amino-L-phenylalamine + 28 mg EL4 immunoglobulin | 80% mice surviving at 42 days |

Drug-antibody complexes according to the present invention are shown to provide considerably greater protection of mice than either the immuno EL4 globulin alone or the drug attached to non-specific globulin. In addition the equivalent doses of the toxic agents alone are lethal for mice whereas the maximum tolerated dose of drug used alone is insufficient to significantly affect the outcome under the conditions of the present test.

What is claimed is:

1. An antitumor agent comprising p-di(2-chloroethyl)amino-L-phenylalanine or N,N-bis(2-chloroethyl)p-phenylenediamine hydrochloride as a cytotoxic agent bound to a tumor specific antibody by peptide bonds.

2. An antitumor agent according to claim 1 having 5–15 molecules of cytotoxic agent per molecule of tumor specific antibody.

3. An antitumor agent according to claim 1 comprising p-di(2-chloroethyl)amino-L-phenylalamine bound to antibodies specific against EL4 lymphoma by peptide bonds.

4. An antitumor agent according to claim 1 comprising N,N-bis(2-chloroethyl)p-phenylenediamine bound to antibodies specific against EL4 lymphoma by peptide bonds.

* * * * *